United States Patent
Roach et al.

(10) Patent No.: US 10,271,954 B2
(45) Date of Patent: Apr. 30, 2019

(54) METHODS AND TECHNIQUES FOR TIBIAL IMPLANT PLACEMENT

(71) Applicant: Zimmer, Inc., Warsaw, IN (US)

(72) Inventors: Brian Edward Roach, Osceola, IN (US); Fred A. Wentorf, Warsaw, IN (US); Amanda Szalkowski, Warsaw, IN (US); Vanessa Croll, Warsaw, IN (US); Tyler Bell, Warsaw, IN (US)

(73) Assignee: Zimmer, Inc., Warsaw, IN (US)

(*) Notice: Subject to any disclaimer, the term of this patent is extended or adjusted under 35 U.S.C. 154(b) by 69 days.

(21) Appl. No.: 15/409,254

(22) Filed: Jan. 18, 2017

(65) Prior Publication Data

US 2017/0209278 A1 Jul. 27, 2017

Related U.S. Application Data

(60) Provisional application No. 62/281,796, filed on Jan. 22, 2016.

(51) Int. Cl.
*A61F 2/38* (2006.01)
*A61F 2/30* (2006.01)

(52) U.S. Cl.
CPC ...... *A61F 2/389* (2013.01); *A61F 2002/3092* (2013.01); *A61F 2002/3093* (2013.01); *A61F 2002/30878* (2013.01); *A61F 2002/30884* (2013.01); *A61F 2002/30889* (2013.01); *A61F 2002/30892* (2013.01)

(58) Field of Classification Search
CPC ............ A61F 2/389; A61F 2002/30878; A61F 2002/30884; A61F 2002/30889
See application file for complete search history.

(56) References Cited

U.S. PATENT DOCUMENTS

| | | | | |
|---|---|---|---|---|
| 5,480,444 A | * | 1/1996 | Incavo | A61F 2/389 623/20.32 |
| 2004/0083005 A1 | * | 4/2004 | Jacobsson | A61F 2/389 623/23.44 |

* cited by examiner

*Primary Examiner* — Brian A Dukert
(74) *Attorney, Agent, or Firm* — Schwegman Lundberg & Woessner, P.A.

(57) ABSTRACT

Methods, techniques and apparatuses are disclosed including exemplary methods of performing a knee arthroplasty of the tibia. One exemplary method can include determining at least a depth of a distal fixation feature of a tibial implant, and forming a metaphyseal recess in a proximal portion of the tibia. The recess can be configured to receive the distal fixation feature therein and can be sized to exceed at least the depth of the distal fixation feature such that when a distal surface of the tibial implant contacts a proximal surface of the proximal portion of the tibia and the distal fixation feature is received in the metaphyseal recess, a gap remains between the distal fixation feature and one or more surfaces that form a portion of the metaphyseal recess.

18 Claims, 3 Drawing Sheets

METHODS AND TECHNIQUES FOR TIBIAL IMPLANT PLACEMENT

CLAIM OF PRIORITY

This application claims the benefit of U.S. Provisional Patent Application Ser. No. 62/281,796, filed on Jan. 22, 2016, the benefit of priority of which is claimed hereby, and which is incorporated by reference herein in its entirety.

FIELD

The present subject matter relates to orthopedic procedures and, more particularly, to knee arthroplasty procedures where a tibial implant having one or more distal fixation features is utilized.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial component implanted on the proximal end of a tibia to replicate the function of a healthy natural knee.

Tibial implants (trays) are utilized in various knee arthroplasty procedures such as in unicompartmental, bicompartmental, total (TKA), and total sparing ACL/PCL procedures. Typically, a tibial implant can have a distal side secured to the bone stock of a resected proximal tibia. A bearing component can be secured to an opposing side of the tibial implant. The tibial implant allows the bearing surface to be fixed so as to replicate the anatomical articulation of a knee joint when used in combination with a femoral prosthesis.

OVERVIEW

The present inventors have recognized, among other things, an opportunity for facilitating abutment between a distal surface of a tibial implant and a resected proximal surface of the tibia. More particularly, the present inventors have recognized that traditional fixation features for the tibial implant such as a stem, keel, and/or fins may not be appropriately sized relative to corresponding metaphyseal recesses of the tibia. A result of such incorrect sizing is that the fixation feature(s) can come into contact with one or more surfaces that define the metaphyseal recess(es) prior to the distal surface of the tibial implant coming into contact with (seating on) the resected proximal surface of the tibia. This can result in a reduced ability to achieve bone ingrowth into a porous material present on the distal surface of the tibial implant. The present inventors propose methods and techniques where the metaphyseal recesses of the tibia are appropriately sized to facilitate contact between the distal surface of the tibial implant and the resected proximal surface of the tibia. This can be accomplished by creating a sufficient gap between one or more surfaces of the fixation feature(s) and the one or more surfaces that define the metaphyseal recess(es) such that the one or more surfaces of the fixation feature(s) and the one or more surfaces that define the metaphyseal recess(es) do not come into contact when the distal surface of the tibial implant and the resected proximal surface of the tibia are in abutment.

To further illustrate the methods disclosed herein, the following non-limiting examples are provided:

In Example 1, a method of performing a knee arthroplasty of the tibia, the method can include determining at least a depth of a distal fixation feature of a tibial implant, and forming a metaphyseal recess in a proximal portion of the tibia, the recess can be configured to receive the distal fixation feature therein and can be sized to exceed at least the depth of the distal fixation feature such that when a distal surface of the tibial implant contacts a proximal surface of the proximal portion of the tibia and the distal fixation feature is received in the metaphyseal recess a gap remains between the distal fixation feature and one or more surfaces that form a portion of the metaphyseal recess.

In Example 2, the method of Example 1, wherein determining at least the depth of the distal fixation feature can include determining a size of an interfacing surface of the distal fixation feature along at least one reference dimension.

In Example 3, the method of any one or any combination of Examples 1-2, wherein a size of the distal fixation feature can additionally be determined with respect to one or more of a width and a length of the distal fixation feature.

In Example 4, the method of any one or any combination of Examples 1-3, wherein the metaphyseal recess can be configured such that one or more of a width and a length of the recess exceeds one or more of a corresponding width and a corresponding length of the metaphyseal recess.

In Example 5, the method of any one or any combination of Examples 1-4, wherein the distal surface of the tibial implant can comprise a porous material.

In Example 6, the method of any one or any combination of Examples 1-5, wherein the distal fixation feature can comprise at least one of a peg, a keel, a stem, a rail, and a fin.

In Example 7, a method of performing a knee arthroplasty of the tibia, the method can include resecting a proximal portion of a tibia to form a proximal surface thereon, determining a size of a distal fixation feature of a tibial implant, forming a metaphyseal recess in the proximal portion of the tibia, the recess configured to receive the distal fixation feature therein and sized to exceed the size of the distal fixation feature at a maximum tolerance with the recess at a minimum tolerance, and seating the tibial implant on the proximal surface such that when a distal surface of the tibial implant contacts the proximal surface and the distal fixation feature is received in the metaphyseal recess a gap remains between the distal fixation feature and one or more surfaces that form at least a portion of the metaphyseal recess.

In Example 8, the method of Example 7, wherein determining the size of the distal fixation feature can include determining a size of an interfacing surface of the distal fixation feature along at least one reference dimension.

In Example 9, the method of Example 8, wherein the size of the interfacing surface can be determined with respect to one or more of a width, a depth, and a length of the distal fixation feature.

In Example 10, the method of any one or any combination of Examples 7-9, wherein the metaphyseal recess can be configured such that at least a depth and one or more of a width and a length of the recess exceeds a corresponding depth and one or more of a corresponding width and a corresponding length of the metaphyseal recess.

In Example 11, the method of any one or any combination of Examples 7-10, wherein the distal surface of the tibial implant can comprise a porous material.

In Example 12, the method of any one or any combination of Examples 7-11, wherein the distal fixation feature can comprise at least one of a peg, a keel, a stem, a rail, and a fin.

In Example 13, a method of performing a knee arthroplasty of the tibia, the method can include forming a metaphyseal recess in a proximal portion of the tibia, the recess configured to receive a distal fixation feature of a tibial implant therein, and seating the tibial implant on the proximal surface such that when a distal surface of the tibial implant contacts a proximal surface of the proximal portion of the tibia and the distal fixation feature is received in the metaphyseal recess a gap remains in at least a depth direction between the distal fixation feature and one or more surfaces that form a portion of the recess, wherein the gap remains even at maximum tolerance of the distal fixation feature and a minimum tolerance of the recess.

In Example 14, the method of Example 13, can further comprise determining a size of an interfacing surface of the distal fixation feature along at least one reference plane.

In Example 15, the method of any one or any combination of Examples 13-14, wherein a size of the distal fixation feature can additionally be determined with respect to one or more of a width and a length of the distal fixation feature.

In Example 16, the method of any one or any combination of Examples 13-15, wherein the metaphyseal recess can be configured such that one or more of a width and a length of the recess exceeds one or more of a corresponding width and a corresponding length of the metaphyseal recess.

In Example 17, the method of any one or any combination of Examples 13-16, wherein the distal surface of the tibial implant can comprise a porous material.

In Example 18, the method of any one or any combination of Examples 13-17, wherein the distal fixation feature can comprise at least one of a peg, a keel, a stem, a rail, and a fin.

In Example 19, the methods of any one or any combination of Examples 1-18 can optionally be configured such that all elements or options recited are available to use or select from.

These and other examples and features of the present methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

Figure 1:
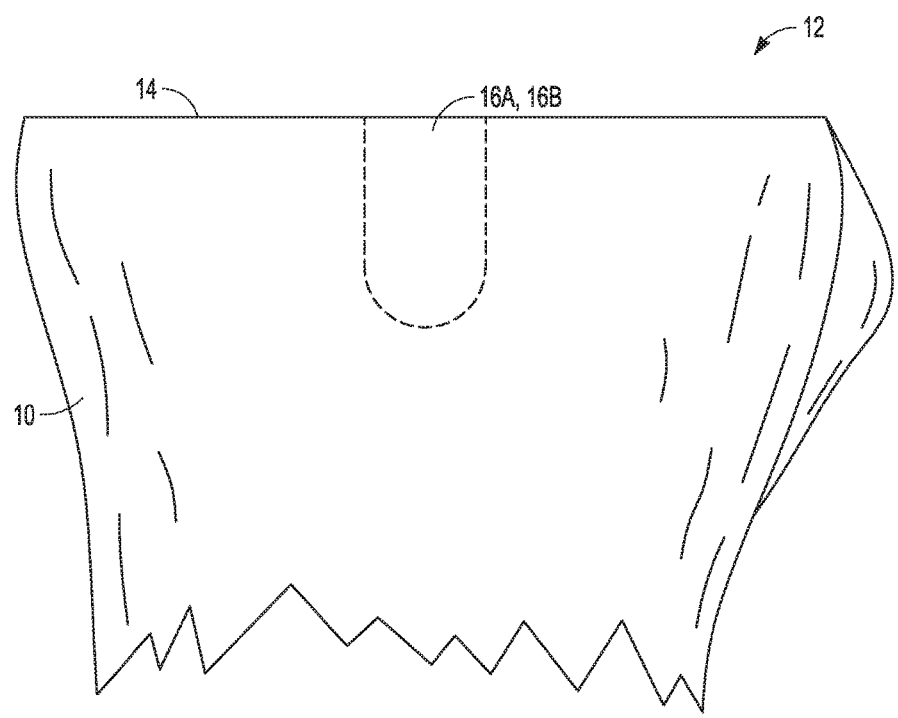
FIG. 1 is a side view of a proximal tibia following resection according to an example of the present application.

It has typically been the practice with tibial implants that do not utilize bone cement for fixation to closely match the size and shape including a depth of a metaphyseal recess in a proximal portion of the tibia to a corresponding size and shape of a distal fixation feature of a tibial implant. This practice is used to maximize surface area available for bone ingrowth/ongrowth into a porous material that can cover the portions of the distal fixation feature in addition to a distal surface of a baseplate of the tibial implant. By maximizing surface area available for bone ingrowth/ongrowth into the porous material, a maximum fixation of the tibial implant to the tibia can be achieved. However, the present inventors recognize that sizing the distal fixation feature and the metaphyseal recess appropriately, considering implant/surgical instrument tolerances and variations in surgical technique, can be difficult to achieve. As a result, in some cases the distal fixation feature can "bottom out" or otherwise come into contact with one or more surfaces that form of the metaphyseal recess prior to the tibial implant fully seating down onto a resected proximal surface of the tibia (i.e. the distal surface of the baseplate of the tibial implant does not contact the resected proximal surface of the tibia but instead has a gap therebetween). The result of such miss-sizing can be a much reduced surface area between the tibial implant and the tibia to facilitate bone ingrowth/ongrowth as well as a final tibial implant/tibia construction that can be more sensitive to excessive implant micro-motion which can also limit bone ingrowth/ongrowth success.

In view of the foregoing, the present inventors propose methods of performing a knee arthroplasty of the tibia. One method can include determining at least a depth of a distal fixation feature of a tibial implant, and forming a metaphyseal recess in a proximal portion of the tibia. The recess can be configured to receive the distal fixation feature therein and can be sized to exceed at least the depth of the distal fixation feature such that when a distal surface of the tibial implant contacts a proximal surface of the proximal portion of the tibia and the distal fixation feature is received in the metaphyseal recess, a gap remains between the distal fixation feature and one or more surfaces that form a portion of the metaphyseal recess.

In a total knee arthroplasty (referred to simply as a "TKA") both of the medial and lateral condyles of the femur can be resected. Similarly, the tibia can be resected to remove the medial articular surface and the lateral articular surface using a cutting apparatus. Other portions of the knee, e.g., the intercondylar eminence, ACL can also be removed. Depending on the type of TKA, features such as the PCL can be spared or can also be removed. Prostheses can be implanted on the femur and the tibia providing for the replaced articular surfaces. Although shown in reference to a TKA and corresponding implant, the techniques and methods described herein are also applicable to other knee arthroplasty procedures such as a partial knee arthroplasty (e.g., a unicompartmental knee arthroplasty).

FIG. 1 shows a proximal end portion 10 of the tibia 12 after having been resected for a TKA. The proximal end portion 10, after being resected, can include a proximal surface 14. Although not illustrated in FIG. 1, the proximal surface 14 can in some cases be sloped varus-valgus and/or anterior-posterior. One or more metaphyseal recess(es) 16A, 16B can be formed in the proximal end portion with surgical instruments (e.g., a chisel, a drill, a broach, or the like). The metaphyseal recess 16 can have an opening at the proximal surface 14 and can extend proximal-distal, medial-lateral, and/or anterior-posterior within the proximal end portion 10.

Figure 2:
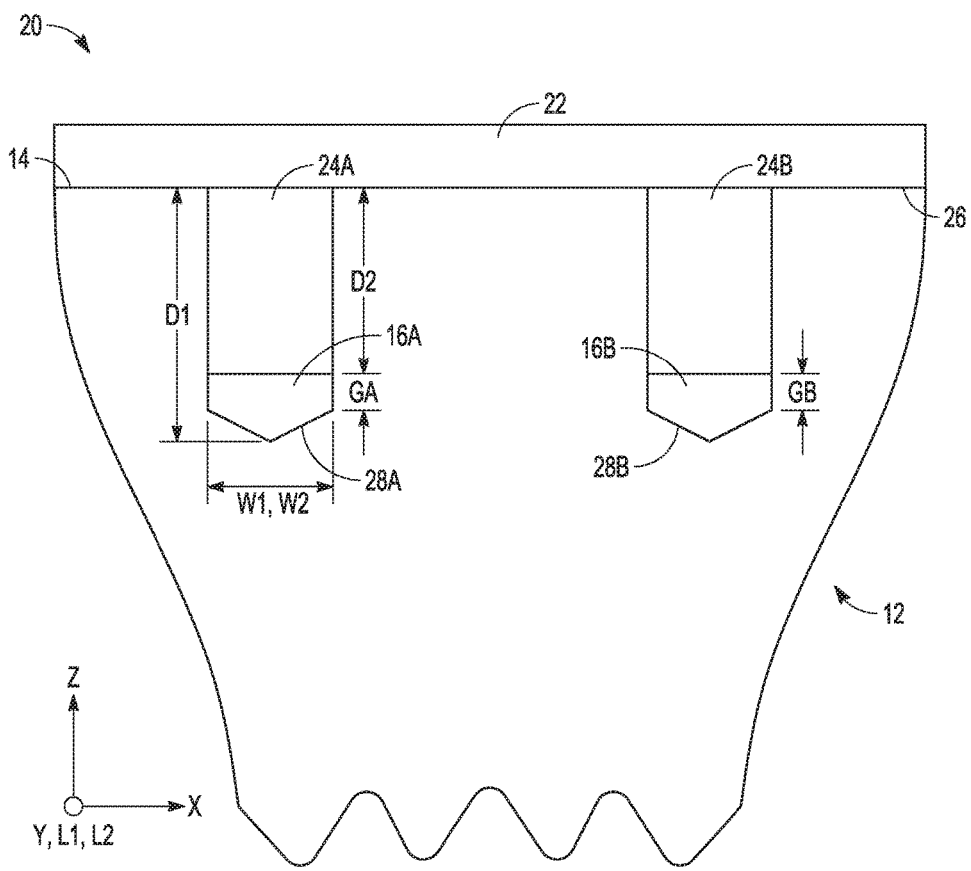
FIG. 2 is a cross-sectional view of the proximal tibia of FIG. 1 with a tibial implant seated thereon and gaps between distal fixation features and metaphyseal recesses according to an example of the present application.

FIG. 2 shows a cross-section of a tibial implant 20 seated on the proximal end portion 10 of the tibia 12 according to one example of the present disclosure. In particular, FIG. 2 provides a view of the tibial implant 20 and the proximal end portion 10 of the tibia 12 in a coronal plane.

In FIG. 2, the tibial implant 20 can include a baseplate 22 and distal fixation features 24A and 24B. The baseplate 22 can include a distal surface(s) 26 configured to mate with the resected proximal surface 14 of the tibia 12. The distal fixation features 24A and 24B can comprise pegs as shown in FIG. 2. However, in other examples the distal fixation features 24A and 24B can comprise any one of a peg, a keel, a stem, a rail, and a fin, for example.

As discussed previously, the metaphyseal recesses 16A, 16B extend into the proximal end portion 10 and can be configured to receive the distal fixation features 24A, 24B therein. The metaphyseal recesses 16A, 16B can be sized to exceed at least the depth of the distal fixation feature 24A, 24B when the distal fixation features 24A, 24B are at a maximum tolerance and the metaphyseal recesses 16A, 16B are at a minimum tolerance. Thus, gaps GA and GB can remain between each of the distal fixation features 24A, 24B and corresponding surfaces 28A, 28B that form a portion of each of the metaphyseal recesses 16A, 16B. Each of the distal fixation features 24A, 24B can have a size and shape in three dimensions (using a Cartesian coordinate system) comprising a width W1 (X), a length L1 (Y), and a depth D1 (Z). Similarly, each of the metaphyseal recesses 16A, 16B can have a size and shape in three dimensions (using a Cartesian coordinate system) comprising a width W2 (X), a length L2 (Y), and a depth D2 (Z). The size and shape of the distal fixation features 24A and 24B can vary relative to each other or can be substantially the same as shown in the example of FIG. 2. Similarly, gaps GA and GB need not be substantially similar in size as illustrated but can vary from one another in other examples.

As shown in FIG. 2, the tibial implant 20 can be seated such that the distal surface 26 abuts the proximal surface 14. In such position, the recesses 16A, 16B can receive the distal fixation features 24A, 24B therein and can be sized with the depth D2 to exceed at least the depth D1 of the distal fixation features 24A, 24B. Thus, when the distal surface 26 of the tibial implant 20 contacts the proximal surface 14 of the proximal portion 10 of the tibia 12 and each distal fixation feature 24A, 24B is received in the corresponding metaphyseal recess 16A, 16B, the gaps GA, GB remain between each distal fixation feature 24A, 24B and the one or more corresponding surfaces 28A, 28B that form a portion of each metaphyseal recess 16A, 16B. Put another way, the depth D2 of the metaphyseal recesses 16A, 16B can exceed the depth D1 of the distal fixation features 24A, 24B even with the distal fixation features 24A, 24B at a maximum tolerance and the metaphyseal recesses 16A, 16B are at a minimum tolerance (hence gaps GA and GB) such that the tibial implant 20 can be seated such that the distal surface 26 abuts the proximal surface 14. As shown in FIG. 2, in some examples the width W1 and the width W2 can be substantially similar to create a desired fixation for the tibial implant 20. In other examples the length L1 and the length L2 can be substantially similar. However, in yet other examples such as the one of FIG. 3, at least one of the length L2 and the width W2 can exceed that of the length L1 and the width W1 even with the distal fixation features 24A, 24B are at a maximum tolerance and the metaphyseal recesses 16A, 16B are at a minimum tolerance.

Figure 3:
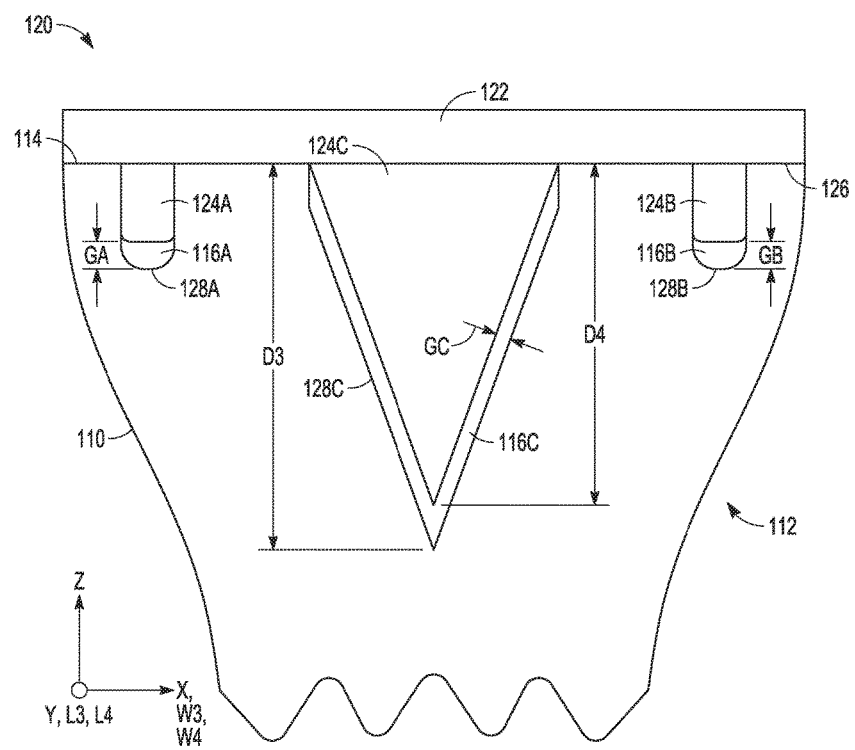
FIG. 3 is a cross-sectional view of another example of an arrangement of a proximal tibia and a tibial implant according to an example of the present application.

FIG. 3 shows a cross-section of a tibial implant 120 seated on a proximal end portion 110 of a tibia 112 according to another example of the present disclosure. In particular, FIG. 3 provides a view of the tibial implant 120 and the proximal end portion 110 of the tibia 112 in a coronal plane similar to FIG. 2.

In FIG. 3, the tibial implant 120 can include a baseplate 122 and distal fixation features 124A, 124B and 124C. The baseplate 122 can include a distal surface(s) 126 configured to mate with the resected proximal surface 114 of the tibia 112. The distal fixation features 124A and 124B can comprise pegs while the distal fixation feature 124C can comprise a keel and fins. However, in other examples the distal fixation features 124A, 124B and/or 124C can comprise any one of a peg, a keel, a stem, a rail, and a fin, for example.

The construction and arrangement of the tibial implant 120 to mount on the proximal end portion 110 has been discussed previously with regard to FIG. 2, and therefore, will not be discussed in great detail. Metaphyseal recesses 116A, 116B, 116 can extend into the proximal end portion 110 and can be configured to receive the distal fixation features 124A, 124B, and 124C therein. The metaphyseal recesses 116A, 116B can sized to exceed at least the depth of the distal fixation feature 124A, 124B when the distal fixation features 124A, 124B are at a maximum tolerance and the metaphyseal recesses 116A, 116B are at a minimum tolerance. Similarly, the metaphyseal recess 116C can have a depth D3 that exceeds at least a depth D4 of the fixation feature 124C along a series of reference planes. A size of the distal fixation feature (e.g., fixation feature 124C) can additionally be determined with respect to one or more of the width W4 and the length L4 of the distal fixation feature 124C. The metaphyseal recess 116C can be sized with one or both of a width W3 and a length L3 to exceed one or more of the width W4 and the length L4 of the distal fixation feature 124C when the distal fixation feature 124C is at a maximum tolerance and the metaphyseal recess 116C is at a minimum tolerance. Thus, gaps GA, GB and GC can remain between each of the distal fixation features 124A, 124B, and 124C and corresponding surfaces 128A, 128B and 128C that form a portion of each of the metaphyseal recesses 116A, 116B, and 116C.

As shown in FIG. 3, the tibial implant 120 can be seated such that the distal surface 126 abuts the proximal surface 114. In such position, the recesses 116A, 116B and 116C can receive the distal fixation features 124A, 124B and 124C therein and can be sized to exceed a size of the distal fixation features 124A, 124B and 124C in one or more of a depth, a width and/or a length. Thus, when the distal surface 126 of the tibial implant 120 contacts the proximal surface 114 of the proximal portion 110 of the tibia 112 and each distal fixation feature 124A, 124B and 124C is received in the corresponding metaphyseal recess 116A, 116B and 116C the gaps GA, GB and GC remain between each distal fixation feature 124A, 124B and the one or more corresponding surfaces 128A, 128B and 128C that form a portion of each metaphyseal recess 116A, 116B and 116C. Put another way, the size of the metaphyseal recesses 116A, 116B and 116C can exceed the size of the distal fixation features 124A, 124B and 124C even with the distal fixation features 124A, 124B and 124C at a maximum tolerance and the metaphyseal recesses 116A, 116B and 116B at a minimum tolerance (hence gaps GA, GB and GC) such that the tibial implant 120 can be seated so that the distal surface 126 abuts the proximal surface 114.

According to one exemplary method of performing a knee arthroplasty of the tibia, the method can include determining at least a depth of a distal fixation feature of a tibial implant, and forming a metaphyseal recess in a proximal portion of the tibia. The recess can be configured to receive the distal fixation feature therein and can be sized to exceed at least the depth of the distal fixation feature such that when a distal surface of the tibial implant contacts a proximal surface of the proximal portion of the tibia and the distal fixation feature is received in the metaphyseal recess, a gap remains between the distal fixation feature and one or more surfaces that form a portion of the metaphyseal recess.

Further examples related to the above method can include any one or any combination of the following: determining at least the depth of the distal fixation feature can include determining a size of an interfacing surface of the distal fixation feature along at least one reference dimension; a size of the distal fixation feature can be additionally determined with respect to one or more of a width and a length of the distal fixation feature; the metaphyseal recess can be configured such that one or more of a width and a length of the recess exceeds one or more of a corresponding width and a corresponding length of the metaphyseal recess; the distal surface of the tibial implant can comprise a porous material; and/or the distal fixation feature can comprise at least one of a peg, a keel, a stem, a rail, and a fin.

According to another exemplary method of performing a knee arthroplasty of the tibia, the method can include resecting a proximal portion of a tibia to form a proximal surface thereon, determining a size of a distal fixation feature of a tibial implant, forming a metaphyseal recess in the proximal portion of the tibia, the recess can be configured to receive the distal fixation feature therein and can be sized to exceed the size of the distal fixation feature at a maximum tolerance with the recess at a minimum tolerance, and seating the tibial implant on the proximal surface such that when a distal surface of the tibial implant contacts the proximal surface and the distal fixation feature can be received in the metaphyseal recess a gap remains between the distal fixation feature and one or more surfaces that form at least a portion of the metaphyseal recess.

Further examples related to the above method can include any one or any combination of the following: determining the size of the distal fixation feature can include determining a size of an interfacing surface of the distal fixation feature along at least one reference dimension; the size of the interfacing surface can be determined with respect to one or more of a width, a depth, and a length of the distal fixation feature; the metaphyseal recess can be configured such that at least a depth and one or more of a width and a length of the recess exceeds a corresponding depth and one or more of a corresponding width and a corresponding length of the metaphyseal recess; the distal surface of the tibial implant can comprise a porous material; and/or the distal fixation feature can comprise at least one of a peg, a keel, a stem, a rail, and a fin.

According to another exemplary method of performing a knee arthroplasty of the tibia, the method can include forming a metaphyseal recess in a proximal portion of the tibia, the recess configured to receive a distal fixation feature of a tibial implant therein, and seating the tibial implant on the proximal surface such that when a distal surface of the tibial implant contacts a proximal surface of the proximal portion of the tibia and the distal fixation feature can be received in the metaphyseal recess, a gap remains in at least a depth direction between the distal fixation feature and one or more surfaces that form a portion of the recess, wherein the gap can remain even at maximum tolerance of the distal fixation feature and a minimum tolerance of the recess.

Further examples related to the above method can include any one or any combination of the following: determining a size of an interfacing surface of the distal fixation feature along at least one reference plane, a size of the distal fixation feature can additionally be determined with respect to one or more of a width and a length of the distal fixation feature, the metaphyseal recess can be configured such that one or more of a width and a length of the recess exceeds one or more of a corresponding width and a corresponding length of the metaphyseal recess, the distal surface of the tibial implant comprises a porous material, and/or the distal fixation feature can comprise at least one of a peg, a keel, a stem, a rail, and a fin.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all The claimed invention is:

1. A method of performing a knee arthroplasty of the tibia, the method comprising:
   determining at least a depth of a distal fixation feature of a tibial implant;
   forming a metaphyseal recess in a proximal portion of the tibia, the recess configured to receive the distal fixation feature therein and sized to exceed at least the depth of the distal fixation feature; and
   implanting the tibial implant by inserting the distal fixation feature distally into the metaphyseal recess and contacting a proximal surface of the proximal portion of the tibia with a distal surface of the tibial implant, wherein when implanted and so inserted the distal fixation feature is received in the metaphyseal recess and a gap remains between the distal fixation feature and one or more surfaces that form a portion of the metaphyseal recess.

2. The method of claim 1, wherein determining at least the depth of the distal fixation feature includes determining a size of an interfacing surface of the distal fixation feature along at least one reference dimension.

3. The method of claim 1, wherein a size of the distal fixation feature is additionally determined with respect to one or more of a width and a length of the distal fixation feature.

4. The method of claim 1, wherein the metaphyseal recess is configured such that one or more of a width and a length of the recess exceeds one or more of a corresponding width and a corresponding length of the metaphyseal recess.

5. The method of claim 1, wherein the distal surface of the tibial implant comprises a porous material.

6. The method of claim 1, wherein the distal fixation feature comprises at least one of a peg, a keel, a stem, a rail, and a fin.

7. A method of performing a knee arthroplasty of the tibia, the method comprising:
   resecting a proximal portion of a tibia to form a proximal surface thereon;
   determining a size of a distal fixation feature of a tibial implant;
   forming a metaphyseal recess in the proximal portion of the tibia, the recess configured to receive the distal fixation feature therein and sized to exceed the size of the distal fixation feature at a maximum tolerance with the recess at a minimum tolerance; and
   seating the tibial implant down distally on the proximal surface such that when a distal surface of the tibial implant fully contacts the proximal surface with no gap therebetween, wherein the distal fixation feature is received in the metaphyseal recess and a gap remains between the distal fixation feature and one or more surfaces that form at least a portion of the metaphyseal recess.

8. The method of claim 7, wherein determining the size of the distal fixation feature includes determining a size of an interfacing surface of the distal fixation feature along at least one reference dimension.

9. The method of claim 8, wherein the size of the interfacing surface is determined with respect to one or more of a width, a depth, and a length of the distal fixation feature.

10. The method of claim 7, wherein the metaphyseal recess is configured such that at least a depth and one or more of a width and a length of the recess exceeds a corresponding depth and one or more of a corresponding width and a corresponding length of the metaphyseal recess.

11. The method of claim 7, wherein the distal surface of the tibial implant comprises a porous material.

12. The method of claim 7, wherein the distal fixation feature comprises at least one of a peg, a keel, a stem, a rail, and a fin.

13. A method of performing a knee arthroplasty of the tibia, the method comprising:
   forming a metaphyseal recess in a proximal portion of the tibia by drilling distally into the proximal portion and leaving an opening to the metaphyseal recess at the proximal portion of the tibia, the recess configured to receive a distal fixation feature of a tibial implant therein with the distal fixation feature passing through the opening; and
   seating the tibial implant distally on the proximal surface such that when a distal surface of the tibial implant contacts a proximal surface of the proximal portion of the tibia and the distal fixation feature is received in the metaphyseal recess such that a gap remains in at least a depth direction between the distal fixation feature and one or more surfaces that form a portion of the recess, wherein the gap remains even at maximum tolerance of the distal fixation feature and a minimum tolerance of the recess.

14. The method of claim 13, further comprising determining a size of an interfacing surface of the distal fixation feature along at least one reference plane.

15. The method of claim 13, wherein a size of the distal fixation feature is additionally determined with respect to one or more of a width and a length of the distal fixation feature.

16. The method of claim 13, wherein the metaphyseal recess is configured such that one or more of a width and a length of the recess exceeds one or more of a corresponding width and a corresponding length of the metaphyseal recess.

17. The method of claim 13, wherein the distal surface of the tibial implant comprises a porous material.

18. The method of claim 13, wherein the distal fixation feature comprises at least one of a peg, a keel, a stem, a rail, and a fin.

* * * * *